(12) United States Patent
Nikodem et al.

(10) Patent No.: US 9,068,940 B2
(45) Date of Patent: Jun. 30, 2015

(54) OPTICAL SUBTRACTION OF MOLECULAR DISPERSION SIGNALS ENABLED BY DIFFERENTIAL OPTICAL DISPERSION SPECTROSCOPY

(71) Applicants: Michal Nikodem, Wroclaw (PL); Gerard Wysocki, Princeton, NJ (US)

(72) Inventors: Michal Nikodem, Wroclaw (PL); Gerard Wysocki, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 68 days.

(21) Appl. No.: 14/058,672

(22) Filed: Oct. 21, 2013

(65) Prior Publication Data
US 2014/0111808 A1 Apr. 24, 2014

Related U.S. Application Data

(60) Provisional application No. 61/715,982, filed on Oct. 19, 2012.

(51) Int. Cl.
*G01J 3/45* (2006.01)
*G01N 21/59* (2006.01)
(Continued)

(52) U.S. Cl.
CPC .............. *G01N 21/59* (2013.01); *G01J 3/4338* (2013.01); *G01J 2003/451* (2013.01); *G01N 21/31* (2013.01); *G01N 2021/3133* (2013.01); *G01N 2021/3185* (2013.01)

(58) Field of Classification Search
CPC .............. G01N 2021/3185; G01N 2021/3133; G01N 21/255; G01N 21/59; G01N 21/25; G01N 21/31; G01N 21/61; G01N 2223/0563; G01J 3/42; G01J 2003/421; G01J 2003/423; G01J 3/433; G01J 3/4338; G01J 2003/451; G01J 2003/4538
USPC ................................................. 356/451, 484
See application file for complete search history.

(56) References Cited

U.S. PATENT DOCUMENTS

| 4,847,512 A | 7/1989 | Seta |
| 2005/0094149 A1* | 5/2005 | Cannon .................... 356/437 |

(Continued)

FOREIGN PATENT DOCUMENTS

| EP | 0 920 599 A1 | 6/1999 |
| EP | 1 058 813 A1 | 12/2000 |
| JP | 11-14544 A | 1/1999 |
| WO | WO 98/08047 A1 | 2/1998 |

OTHER PUBLICATIONS

Nikodem, Michal, Remote mid-infrared sensing using Chirped Laser Dispersion Spectroscopy, May 2011, SPIE, vol. 8024, pp. 1-6.*

(Continued)

*Primary Examiner* — Tarifur Chowdhury
*Assistant Examiner* — Michael P Lapage
(74) *Attorney, Agent, or Firm* — Meagher Emanuel Laks Goldberg & Liao, LLP

(57) ABSTRACT

An apparatus and method for differential optical dispersion using a first sample and a second sample are disclosed. The apparatus includes a single frequency chirped laser source configured to generate a single frequency chirped laser beam. A first beam splitter is configured to split the single frequency chirped laser beam into first and second optical branches, the first sample being located in the first optical branch, the second sample being located in the second optical branch. A frequency shifter is located in the second optical branch, downstream of the second sample. A second beam splitter is configured to combine the first and second optical branches and generate a chirp-modulated mixed light beam. A square law detector is configured to detect the chirp-modulated mixed light beam and generate a heterodyne beatnote signal. A demodulator is configured for detection of the heterodyne beatnote signal to generate a transmission/differential optical dispersion spectrum.

11 Claims, 3 Drawing Sheets

(51) Int. Cl.
*G01N 21/31* (2006.01)
*G01J 3/433* (2006.01)

(56) References Cited

U.S. PATENT DOCUMENTS

| 2006/0012797 | A1* | 1/2006 | Chang et al. | 356/484 |
|---|---|---|---|---|
| 2006/0132792 | A1* | 6/2006 | Schultz et al. | 356/480 |
| 2011/0069309 | A1* | 3/2011 | Newbury et al. | 356/326 |
| 2012/0274929 | A1 | 11/2012 | Weidmann et al. | |

OTHER PUBLICATIONS

D. Richter et al., "Development of a tunable mid-IR difference frequency laser source for highly sensitive airborne trace gas detection," Applied Physics B: Lasers and Optics 75, 281-288 (Aug. 2002).

B. Tuzson et al., "Continuous isotopic composition measurements of tropospheric C02 at Jungfraujoch (3580 m a.s.l.), Switzerland: real-time observation of regional pollution events," Atmospheric Chemistry and Physics II, 1685-1696 (2011).

Wysocki et al., "Molecular dispersion spectroscopy for chemical sensing using chirped mid-infrared quantum cascade laser" vol. 18, No. 25/ Optics Express, pp. 26123-26140, Dec. 6, 2010.

Moschella et al., "Resonant, heterodyne laser interferometer for state density measurements in atoms and ions", Review of Scientific Instruments, vol. 77, No. 093108-1, 2006.

Schwarze et al., "Method for obtaining gas concentration with a phase-based metrology system", Applied Optics, XP002621558, vol. 37, No. 18, pp. 3942-3947, Jun. 1998.

Taslakov et al., "Open path atmospheric spectroscopy using room temperature operated pulsed quantum cascade laser", Spectrochimica Acta. Part A, XP025176687, vol. 63, No. 5, pp. 1002-1008, Apr. 2006.

\* cited by examiner

OPTICAL SUBTRACTION OF MOLECULAR DISPERSION SIGNALS ENABLED BY DIFFERENTIAL OPTICAL DISPERSION SPECTROSCOPY

CROSS-REFERENCE TO PRIOR FILED APPLICATIONS

This application claims priority to U.S. provisional application 61/715,982 filed on Oct. 19, 2012 which is incorporated herein in its entirety.

STATEMENT REGARDING FEDERALLY SPONSORED RESEARCH OR DEVELOPMENT

This invention was made with government support under National Science Foundation contract # CMMI-0954897. The government has certain rights in this invention.

FIELD OF THE INVENTION

The present disclosure generally relates to differential optical dispersion using a chirp modulation single frequency laser source.

BACKGROUND

Differential/comparative analysis of two gas samples is often used to perform precise and accurate molecular detection, e.g. in isotopic ratio measurements when sample under test must be compared with a reference standard preferably at the same time. Typically, in such applications two strategies are applied: (i) laser beam is divided into two beams and two photodetectors are used (one for each beam interacting with different sample), or (ii) laser beam is directed through a single gas cell which is filled with a first sample and subsequently is detected using a single photodiode. The process is then repeated with a second gas sample. This process measures an alternated signal originating from both gases. In the first case, the measurement can be affected by the difference in specifications (responsivity, linearity etc.) of both detectors as well as by the uncorrelated drift of any parameters of the two optical branches (thermal drifts affecting the optical system dimensions, difference in optical interference effects observed in each optical arm, electronic or thermal drifts of the electronics etc.). In the second case, switching of the gas mixture inside the gas cell requires a complex gas handling, the cell evacuation process is slow, and any nonlinearity of the detector can also affect measurement results. Due to unavoidable drifts in the system the slow gas exchange process will reduce reliability and long-term stability of the setup. Therefore improved differential/comparative analysis systems are desirable.

SUMMARY OF THE INVENTION

An apparatus and method for differential optical dispersion using a first sample and a second sample are disclosed. The apparatus includes a single frequency chirped laser source configured to generate a single frequency chirped laser beam. A first beam splitter is configured to split the single frequency chirped laser beam into first and second optical branches, the first sample being located in the first optical branch, the second sample being located in the second optical branch. A frequency shifter is located in the second optical branch, downstream of the second sample. A second beam splitter is configured to combine the first and second optical branches and generate a chirp-modulated mixed light beam. A square law detector is configured to detect the chirp-modulated mixed light beam and generate a heterodyne beatnote signal. A demodulator is configured for detection of the heterodyne beatnote signal to generate a differential optical dispersion spectrum.

The apparatus may also include a signal processor configured to perform spectral fitting. The first and second sample have optical transmission spectra and the demodulator may be configured as amplitude detector to measure the transmission spectrum. The transmission spectrum may have a magnitude that is proportional to the optical transmission which is affected by the sum of the optical absorptions from first and second samples. The demodulator may be configured as a frequency detector to measure the differential optical dispersion spectrum. The differential optical dispersion spectrum may have a magnitude that is proportional to the difference between the optical dispersion spectra of the first and second samples.

The first sample may be a reference sample having a known concentration of a gas and the second sample has an unknown concentration of the gas. The signal processor may be configured to analyze the measured transmission spectrum containing information about the sum of sample concentrations and differential optical dispersion spectrum containing information about the difference of sample concentrations. The signal processor may be configured to analyze the measured transmission and dispersion spectra to retrieve sample parameters other than concentration that also affect the measured spectra. The sample parameters may include at least one of temperature, pressure and optical path length. The frequency shifter may be an acousto-optical modulator or an electro-optical modulator. The apparatus may include a third beam splitter configured to split the single frequency chirped laser beam into a third optical branch. A third sample may be located in the third optical branch. A second frequency shifter may be located in the third optical branch, downstream of the third sample.

A method for differential optical dispersion using a first sample and a second sample is also disclosed. The method includes splitting a single frequency chirped laser beam into first and second optical branches, the first sample being located in the first optical branch, the second sample being located in the second optical branch. A frequency shifter is located in the second optical branch, downstream of the second sample. The first and second optical branches are combined to generate a chirp-modulated mixed light beam. The chirp-modulated mixed light beam is detected to generate a heterodyne beatnote signal. The heterodyne beatnote signal is demodulated to generate a differential optical dispersion spectrum.

The method may also include performing spectral fitting on the transmission spectrum and the differential optical dispersion spectrum. Both the transmission spectrum and the differential optical dispersion spectrum spectra are measured simultaneously with two demodulators configured as amplitude detector and as frequency detector respectively. The first and second sample have optical transmission spectra. The transmission spectrum may have a magnitude that is proportional to the optical transmission which is affected by the sum of the optical absorptions from first and second samples. The differential optical dispersion spectrum may have a magnitude that is proportional to the difference between the optical dispersion spectra of the first and second samples.

The first sample may be a reference sample having a known concentration of a gas and the second sample has an unknown concentration of the gas. The measured transmission spectrum may contain information about the sum of sample concentrations and differential optical dispersion spectrum may contain information about the difference of sample concentrations. The measured transmission and dispersion spectra may be analyzed to retrieve sample parameters other than concentration that also affect the measured spectra. The sample parameters may include at least one of temperature, pressure and optical path length. The frequency shifter is at least one of an acousto-optical modulator and an electro-optical modulator. A third beam splitter may be provided to split the single frequency chirped laser beam into a third optical branch. A third sample may be located in the third optical branch. A second frequency shifter may be located in the third optical branch, downstream of the third sample. The first, second and third optical branches may be combined to generate the chirp-modulated mixed light beam.

BRIEF DESCRIPTION OF THE FIGURES

FIG. 2b is a graph showing the data calculated for the individual concentrations in both cells (C1 and C2) based on the measured sum of $N_2O$ concentrations (CS) and difference in $N_2O$ concentrations (CD) shown in FIG. 2a;

DETAILED DESCRIPTION

Figure 1A:
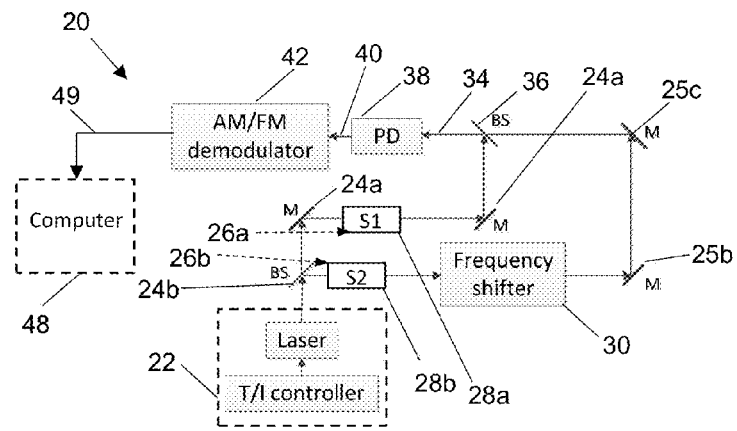
FIG. 1a is block diagram of an apparatus configured for differential/comparative analysis of two gas samples.

Disclosed are a method and apparatus for the optical subtraction of molecular dispersion signals enabled by differential optical dispersion spectroscopy (DODiS). Using the method and apparatus disclosed herein, two samples can be measured simultaneously in exactly the same conditions and using only one optical detector which provides enough information to characterize concentrations of the samples in both optical paths. FIG. 1a is block diagram of an apparatus 20 configured for differential/comparative analysis of two gas samples. The system is coupled to a single frequency chirped laser source 22 configured to generate laser radiation having a fundamental frequency. In this example a distributed feedback (DFB) quantum cascade laser (QCL) and T/I (temperature/current) controller was used. It should be understood that other laser sources may be used without departing from the scope of this disclosure. The laser radiation is divided into two beams (two optical branches) using beam splitter 24b. Each beam interacts with a separate gas sample. In the first optical branch 26a, the beam interacts with sample S1 as shown by reference number 28a. In the second optical branch 26b, the beam interacts with sample S2 as shown by reference number 28b. It should be understood that other optical components may be used to direct the first and second optical branches depending on the desired geometry for the branch, e.g., mirrors 24a and 25a-25c. The second optical branch includes a frequency shifter 30 downstream of (after) the sample S2. The frequency shifter 30 is configured to shift the laser radiation by a frequency shift $\Delta f$ above or below the fundamental frequency. In this example an acousto-optical modulator, AOM is used. It should be understood that other frequency shifters such as an electro-optical modulator may be used without departing from the scope of this disclosure.

The beams from the first and second optical branches 26a, 26b are then recombined into a single dual-frequency beam 34 using beam splitter 38. The dual-frequency beam 34 is detected by a single fast square law photodetector 38 configured to convert the optical dual-frequency beam 34 into an electrical beatnote (heterodyne) signal 40. The frequency shift $\Delta f$ provided by the frequency shifter 30 enables heterodyne detection of the beatnote signal 40 using an AM/FM-demodulator 42. The signal demodulation approach disclosed herein is similar to chirped laser dispersion spectroscopy (CLaDS) disclosed in US Patent Publication 2012-0268746 entitled "Chirp Modulation-Based Detection of Chirped Laser Molecular Dispersion Spectra" which is incorporated herein in its entirety. The output 49 of the demodulator 42 is then coupled to a signal processor for 48 processing of the differential optical dispersion spectrum.

Figure 1B:
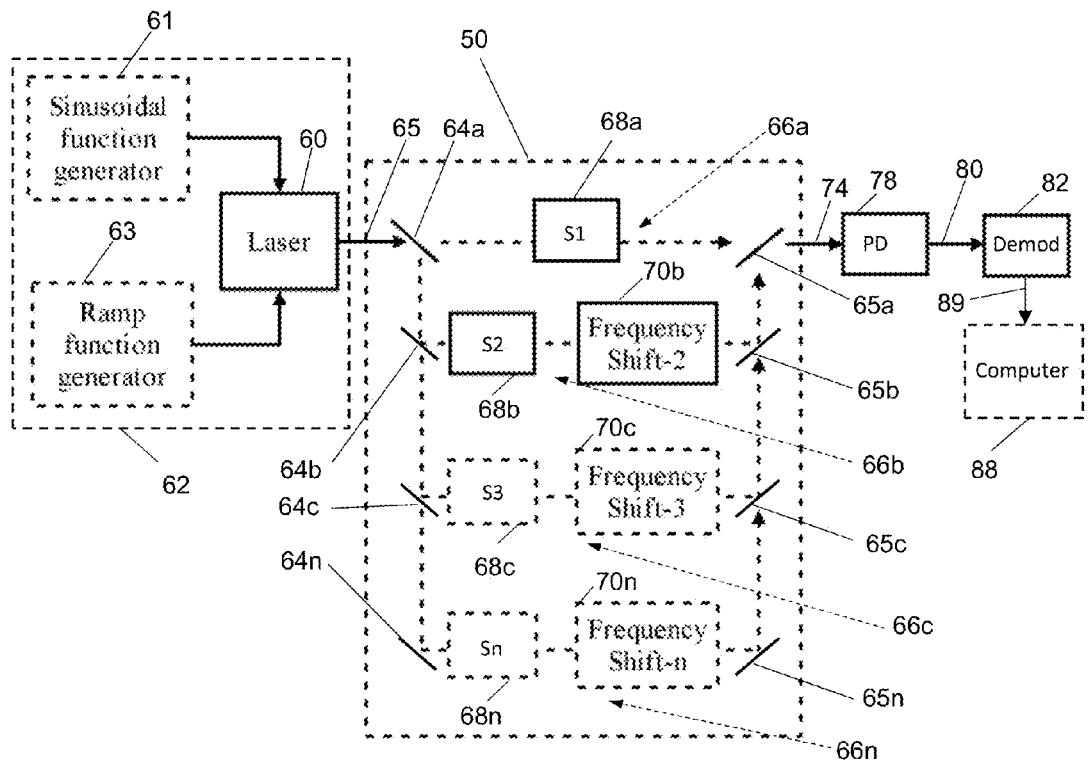
FIG. 1b is a more generalized block diagram of an apparatus configured for differential/comparative analysis of two or more gas samples.

FIG. 1b is a more generalized block diagram of an apparatus 50 configured for differential/comparative analysis of two or more gas samples. In this example, the single frequency chirped laser source 62 includes a laser 60 and a function generator configured to generate a single frequency chirped laser beam 65. For example, a sinusoidal function generator 61 having a modulation frequency f may be used to modulate the laser as discussed in US Patent Publication 2012-0268746 entitled "Chirp Modulation-Based Detection of Chirped Laser Molecular Dispersion Spectra." In the alternative a ramp function generator 63 may be used to scan the beam from single frequency chirped laser source 52 over a range of frequencies as discussed above. See e.g., G. Wysocki and D. Weidmann, "Molecular dispersion spectroscopy for chemical sensing using chirped midinfrared quantum cascade laser," Opt. Express, vol. 18, pp. 26123-26140, 2010 and International Application No.: PCT/GB2010/002095 entitled "Detecting Species in A Dilute Medium" both of which are incorporated herein in their entirety. It should be understood that other techniques to provide single frequency chirped laser source may be used without departing from the scope of this disclosure.

The single frequency chirped laser beam 65 is directed into a beam splitter 64a that splits the laser output into two beams. In this example, multiple optical branches 66a, 66b, 66c, 66n are established using multiple beam splitters 64b and 64c and mirror 64n. It should be understood that at least two optical branches, each with an associated sample, are needed for the differential optical dispersion approach disclosed herein. However, additional optical branches each having an associated sample, e.g., $3^{rd}$, $4^{th}$ . . . $n^{th}$ may be added in a similar fashion as shown in FIG. 1b. A frequency shifter 70b, 70c, 70n is introduced in the second and subsequent optical branch. Each optical branch also has a different frequency shift $\Delta f$. As explained above, the frequency shifter may be an AOM, electro-optical modulator or the like. Beam combiner 65a, 65b, 65c combine the two outputs from the optical branches to generate a chirp-modulated multi-frequency laser beam 74.

The chirp-modulated multi-frequency light beam 74 is detected by a single fast square law photodetector 78 configured to convert the optical chirp-modulated multi-frequency light beam 74 into an electrical beatnote signal 80. The frequency shift Δf provided by the frequency shifters 70b, 70c, 70n enable heterodyne detection of beatnote signals 80 using an AM/FM-demodulator 82. The output 89 of the demodulator 82 is then coupled to a signal processor for 88 processing of differential optical dispersion spectra.

An important difference between prior techniques and the techniques disclosed herein is that the frequency shifter is used after the interaction with the sample which allows for direct comparison of both dispersion signatures. That is, both samples interact with the same laser frequency. When laser radiation is frequency-chirped across the target molecular transition, molecular dispersion affects the frequency of the heterodyne beatnote signal recorded with photodetector 38. The differential optical dispersion spectrum can be retrieved after FM-demodulation of the beatnote and the magnitude of the instantaneous beatnote frequency is proportional to the difference between concentrations in two gas samples. Simultaneously, AM-demodulation can provide information about the total absorption occurring in both samples.

An advantage of the approach disclosed herein is ability to directly subtract the dispersion signals originating from two gas cells (S1 and S2). This may be performed using a heterodyne Mach-Zehnder interferometer formed with two beam-splitters. The optical frequency in one of the interferometer arms is shifted after the light passes through a gas sample, which assures that the radiation passing through both samples has the same optical frequency.

Using similar methodology as the one presented in Wysocki and D. Weidmann. "Molecular dispersion spectroscopy for chemical sensing using chirped midinfrared quantum cascade laser," Opt. Express, vol. 18, pp. 26123-28140, 2010 and International Application No: PCT/GB2010/002095 entitled "Detecting Species in A Dilute Medium", one can derive the following formulas describing dispersion and transmission spectra, respectively:

$$f(\omega) = \frac{1}{2\pi}\left[\Omega + \frac{S \cdot \Delta L}{c} - \frac{S \cdot L_c}{c} \cdot \omega \cdot \left(\frac{dn_1}{d\omega}\bigg|_\omega - \frac{dn_2}{d\omega}\bigg|_\omega\right)\right], \quad (1a)$$

$$A(\omega) = 2E_1 E_2 \exp[-L_c \cdot (\alpha_1(\omega) + \alpha_2(\omega))], \quad (1b)$$

where S is the chirp rate. $L_c$ is the gas cells length, $E_1$ and $E_2$ are the amplitudes of two electromagnetic waves, $n_{1,2}$ are the refractive indexes and $\alpha_{1,2}$ are the absorption coefficients of the media in cells #1 and #2, respectively. ΔL is a path length difference between interferometer arms that can lead to formation of a baseline in dispersion spectrum if ΔL≠0. By using optical delay line within interferometer setup one can set ΔL=0 and baseline will be suppressed. An important property of the proposed DODiS setup is that recorded dispersion spectrum is simply the difference of dispersion signals ($dn_1/d\omega - dn_2/d\omega$) from both samples, whereas transmission profile contains sum of absorptions ($\alpha_1 - \alpha_2$) caused by the two gas samples.

Ways of determining gas samples composition:
1) Measured dispersion and transmission spectra can be fitted using a line by line spectral simulation based on spectroscopic database (e.g. HITRAN) to determine concentrations $C_S$ (from transmission spectrum) and $C_D$ (from dispersion profile). When both sum ($C_S=C_1+C_1$) and difference ($C_D=C_2-C_1$) of concentrations are retrieved, concentration in each sample ($C_1$ and $C_2$) can be easily determined as $C_1=(C_S+C_D)/2$ and $C_1=(C_S-C_D)/2$.
2) If only the ratio $R_C=C_1/C_2$ needs to be determined it is not necessary to use any spectroscopic database to retrieve $C_1$ and $C_2$. Using Kramers-Kronig relation absorption/transmission spectrum can be transformed into dispersion signal and its amplitude $A_S$ can be measured, that corresponds to sum of concentrations ($A_S \propto C_S = C_1 + C_1$). $A_D$ is the amplitude of dispersion spectra measured directly with DODiS and it corresponds to difference of concentrations ($A_D \propto C_D = C_1 - C_2$). Amplitudes of two spectra obtained in this way can be used to calculate $R_C$ as $R_C = C_1/C_2 = (A_S - A_D)/(A_S + A_D)$.
3) If only the ratio $R_C = C_1/C_2$ needs to be determined, where sample #2 is a known reference, one can rely on dispersion measurement only. Firstly, signal from gas sample #2 should be recorded and its amplitude $A_2$ should be measured ($A_2$ is proportional to $C_2$). After amplitude of dispersion signal from reference gas is known, gas cell #1 can be filled with sample to be measured. From that point only signal that corresponds to concentration difference $C_D = C_1 - C_2$ is measured. Its amplitude $A_D$ (proportional to $C_D$) can be used to calculate ratio as $R_C = C_1/C_2 = A_1/A_2 = (A_D + A_2)/A_2 = A_D/A_2 + 1$.

Second application of the disclosed system is the concentration measurement in presence of molecular features that can interfere with the target transition. In such a case one gas cell contains molecule A that is to be measured and molecule B which produces an unwanted spectroscopic 'background'. By filling the other cell with adequate gas mixture containing appropriate amount of molecule B, background spectral features can be suppressed in the differential dispersion spectrum. This will enable precise sensing of the target molecule A.

The proposed system is an actual device and a process of device application (e.g. a specific way of data acquisition and analysis). DODiS has clear fundamental differences with respect to CLaDS in which the sample and reference cannot be directly compared/subtracted (i.e. CLaDS spectra from two samples are spectrally shifted with respect to each other and a proper subtraction is not possible). In the DODiS setup described here both samples are probed with the laser radiation of exactly the same optical frequency. As a result a proper subtraction of the dispersion spectra can be obtained.

An important requirement for correct dispersion spectra subtraction is having the same parameters of the target spectroscopic lines (e.g. lineshape, linewidth of the molecular transitions) in both samples. Since those parameters depend on sample pressure, temperature and on samples composition, small differences in sample and reference parameters can be a significant source of measurement error. In practice, all parameters can be precisely controlled to minimize the potential errors.

Figure 2A:
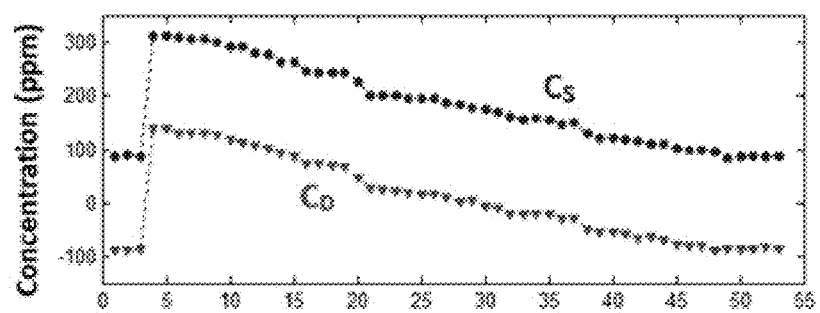
FIG. 2a is a graph showing a sum of $N_2O$ concentrations (CS) retrieved from transmission/absorption spectrum and concentration difference (CD) retrieved from dispersion spectrum after amplitude and frequency demodulation of the beatnote, respectively.
Figure 2B:
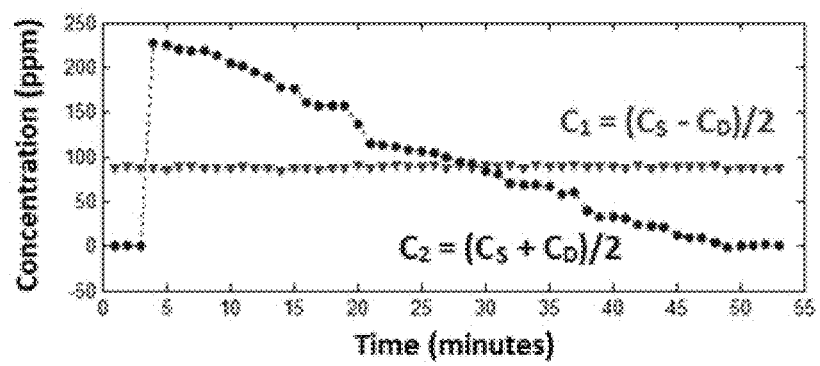

FIG. 2a is a graph showing a sum of $N_2O$ concentrations (CS) retrieved from transmission spectrum and concentration difference (CD) retrieved from dispersion spectrum after amplitude and frequency demodulation of the beatnote, respectively. FIG. 2b is a graph showing the data calculated from the individual concentrations in both cells (C1 and C2). These values were verified experimentally. A continuous wave DFB QCL operating at 4.55 μm was used. This enabled access to the fundamental ro-vibrational transitions of nitrous oxide ($N_2O$). The laser frequency was chirped by applying 10 kHz triangular modulation of the laser current. To show how the addition/subtraction method described here can be used for continuous and simultaneous monitoring of two samples the experiment was performed using two cells filled with different $N_2O$ in $N_2$ mixtures. The first cell remained unaffected during the experiment, while the concentration in the second cell was varied. The second cell was evacuated at the beginning of the experiment and was filled with a mixture of arbitrary concentration after the 3rd measurement. Then the $N_2O$ concentration in the second cell was gradually reduced by dilution with $N_2$ until it contained no $N_2O$ (1 minute delay between each measurement was required to change the $N_2O$ concentration). During this experiment pressure in both cells was controlled at 60 Torr. The HITRAN database was used to fit recorded spectra to determine the sum ($C_S$) and the difference ($C_D$) of the $N_2O$ concentrations. From these data, $C_1$ and $C_2$ concentrations in both cells were calculated. The results are show in FIGS. 2a and 2b and show clearly, that during measurement concentration of $N_2O$ was changed only in the cell #2 while the concentration of $N_2O$ in the cell #1 was constant (approximately 88±1.5 ppm). It is also clear that the concentration $C_1$ calculated as $C_1=(C_S-C_D)/2$ agrees well with the reference measurement performed directly (88.11 ppm from direct absorption data).

Figure 3A:
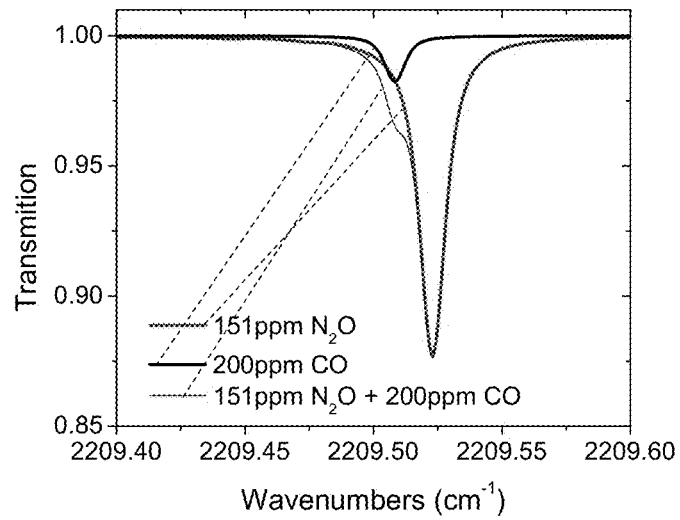
FIG. 3a is a HITRAN simulation of two overlapped spectral lines (strong $N_2O$ and weaker CO) around 2209.5 $cm^{-1}$.

FIG. 3a is a HITRAN simulation of two overlapped spectral lines (strong $N_2O$ and weaker CO) around 2209.5 $cm^{-1}$. This data was verified experimentally. A gas cell was filled with $N_2O$ (151 ppm) and CO (200 ppm) balanced with $N_2$. With QCL operating around 2209.5 $cm^{-1}$ both CO and $N_2O$ absorption lines can be accessed simultaneously. However, two transitions are very close to each other and they partially overlap as shown in FIG. 3a. The goal of the measurement was to determine the amount of CO with the presence of relatively strong $N_2O$ line close-by, which serves as interference gas.

Figure 3B:
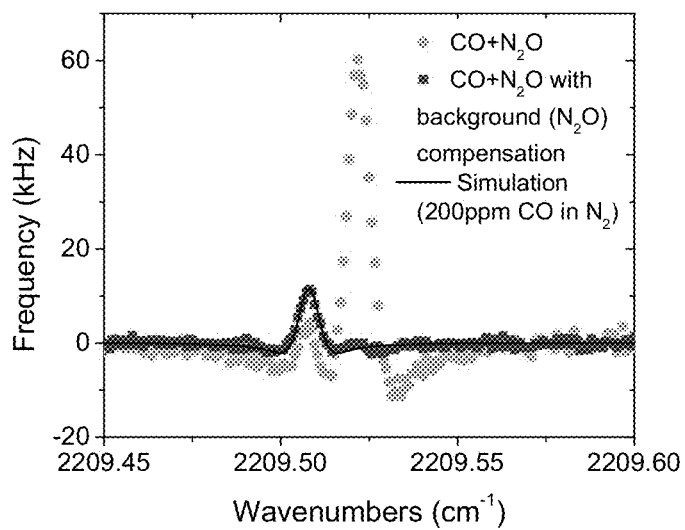
FIG. 3b is a measured dispersion spectrum of gas mixture containing 151 ppm of N2O and 200 ppm of CO in $N_2$ and the same spectrum measured after $N_2O$ line removal using optical subtraction of the interfering spectral feature.

FIG. 3b is a HITRAN simulation of measured dispersion spectrum of gas mixture containing 151 ppm of $N_2O$ and 200 ppm of CO in N2 (cyan) and the same spectrum measured after $N_2O$ line removal using DODiS subtraction of the interfering spectral feature (red—measurement, black—simulation). This fitting of transmission or dispersion spectrum with such a strong spectral interference (as shown in FIG. 3b) is challenging and it is very sensitive to errors in frequency calibration of the spectral scan. Fitting process can be significantly simplified when the interference spectral signature is suppressed optically. In this example, we placed an additional gas cell in second arm of the interferometer. The cell was filled with 151 ppm $N_2O$ balanced with $N_2$. As a result, the stronger $N_2O$ spectral feature became invisible in the dispersion spectrum measured with DODiS which made the fitting process of the weak CO line much simpler (FIG. 3b, red squares—measurement, black line—fitting/simulation using HITRAN database).

By applying the process/device to gas sensing, when two separate samples containing the same molecule are to be measured, the proposed system enables detection of a signal that corresponds to a difference of molecular concentrations in both samples using only one optical detector. By applying the process/device to gas sensing, two signals can be generated: one that corresponds to a sum and second that corresponds to a difference of molecular signals in each sample, when measured separately. As a result, gas concentration in both samples can be determined based on a single measurement using only one optical detector. By applying the process/device to gas sensing, an unwanted background signals originating from unwanted molecular constituents can be suppressed. This significantly simplifies data analysis in the presence of interference from other molecular species.

The techniques disclosed herein may be applied when concentrations of two unknown samples needs to be measured. The concentration of both samples can be retrieved after a single measurement. This will increase the long-term stability of the measurement compared to currently used methods. It should also result in smaller measurement error.

The techniques disclosed herein may be applied when concentrations of one sample needs to be measured with high accuracy through comparison to a known calibrated reference standard (e.g. in isotope ratio measurements the sample must be compared to a calibrated standard). The sample concentration is measured as a ratio of the sample concentration to the reference concentration. This is performed through a direct measurement of a difference in concentrations between the sample and the reference standard as shown in section [0027]. This will increase the long-term stability of the measurement compared to currently used methods. It should also result in smaller measurement error.

The disclosed techniques may be used when molecule concentration has to be determined in the presence of unwanted background transitions (e.g. water vapor, other molecules or other isotopes of the same molecule). By using additional cell filled with appropriate gas mixture at correct pressure and concentration, background transitions can be made invisible in dispersion spectrum. Such background suppression cannot be realized in typically used absorption-based techniques. Some background spectral features can be made invisible when using Faraday rotation spectroscopy but this technique enables measuring only paramagnetic spices (e.g. NO, $NO_2$, OH) and only non-paramagnetic spices are invisible (e.g. water vapor). There is no such limitation in disclosed techniques. The disclosed techniques may be employed by manufacturers of laser equipment and laser sensor systems, e.g., instruments based on TDLAS, WMS, LIDAR etc.

It should be understood that the disclosed systems and methods can be used to perform measurements of other parameters of the samples that can affect the spectrum of the sample. Temperature, pressure, and optical path length are example parameters that can affect the measured transmission and dispersion spectrum. For example if two identical samples are used at exactly the same conditions except sample temperature, the measurement of the differential optical dispersion can be used to retrieve the temperature difference between the samples. Similar differential measurements can be performed for any parameter affecting the transmission and dispersion spectrum of the samples while all other parameters that can affect the spectrum are precisely controlled.

It should be understood that many variations of the disclosed systems and methods are possible based on the disclosure herein. Although features and elements are described above in particular combinations, each feature or element can be used alone without the other features and elements or in various combinations with or without other features and elements. The methods or flow charts provided herein may be at least partially implemented in a computer program, software, or firmware incorporated in a computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks, SSDs and removable disks, magneto-optical media, and optical media such as CD-ROM disks, and digital versatile disks (DVDs).

Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine.

What is claimed is:

1. An apparatus for differential optical dispersion using a first sample and a second sample, the apparatus comprising:
   a single frequency chirped laser source configured to generate a single frequency chirped laser beam;
   a first beam splitter configured to split the single frequency chirped laser beam into first and second optical branches, the first sample being located in the first optical branch, the second sample being located in the second optical branch;
   a frequency shifter located in the second optical branch, downstream of the second sample;
   a second beam splitter configured to combine the first and second optical branches and generate a chirp-modulated mixed light beam;
   a square law detector configured to detect the chirp-modulated mixed light beam and generate a heterodyne beatnote signal; and
   a demodulator configured for demodulation of the heterodyne beatnote signal to generate a differential optical dispersion spectrum.

2. The apparatus of claim 1 further comprising a signal processer configured to perform spectral fitting.

3. The apparatus of claim 1 wherein the demodulator is configured for detection of the heterodyne beatnote signal to generate a transmission spectrum.

4. The apparatus of claim 1 wherein the first and second sample have optical transmission spectra and the demodulator is configured as an amplitude demodulator to generate an output having a magnitude that is proportional to the transmission spectrum which is affected by the sum of the optical absorptions from first and second samples.

5. The apparatus of claim 1 wherein the first and second sample have optical dispersion spectra and the demodulator is configured as a frequency demodulator and the measured differential optical dispersion spectrum have a magnitude that is proportional to the difference between the optical dispersion spectra of the first and second samples.

6. The apparatus of claim 1 wherein the first sample is a reference sample having a known concentration of a gas and the second sample has an unknown concentration of the gas.

7. The apparatus of claim 2 wherein the signal processor is further configured to analyze the measured transmission spectrum containing information about the sum of sample concentrations and differential optical dispersion spectrum containing information about the difference of sample concentrations.

8. The apparatus of claim 2 wherein the signal processor is further configured to analyze the measured transmission and dispersion spectra to retrieve sample parameters other than concentration that also affect the measured spectra.

9. The apparatus of claim 7 wherein the sample parameters include at least one of temperature, pressure and optical path length.

10. The apparatus of claim 1 wherein the frequency shifter is at least one of an acousto-optical modulator and an electro-optical modulator.

11. The apparatus of claim 1 further comprising:
    a third beam splitter configured to split the single frequency chirped laser beam into a third optical branch;
    a third sample located in the third optical branch; and
    a second frequency shifter located in the third optical branch, downstream of the third sample.

* * * * *